(12) United States Patent
Mizus

(10) Patent No.: US 9,597,472 B2
(45) Date of Patent: Mar. 21, 2017

(54) SPIRAL SLIT ENDOTRACHEAL TUBE

(71) Applicant: Irving Mizus, Chevy Chase, MD (US)

(72) Inventor: Irving Mizus, Chevy Chase, MD (US)

( * ) Notice: Subject to any disclaimer, the term of this patent is extended or adjusted under 35 U.S.C. 154(b) by 231 days.

(21) Appl. No.: 14/261,453

(22) Filed: Apr. 25, 2014

(65) Prior Publication Data

US 2015/0306328 A1    Oct. 29, 2015

(51) Int. Cl.
*A61M 16/04* (2006.01)
*A61B 17/24* (2006.01)

(52) U.S. Cl.
CPC .... *A61M 16/0488* (2013.01); *A61M 16/0418* (2014.02); *A61B 2017/242* (2013.01); *A61M 2210/1035* (2013.01)

(58) Field of Classification Search
CPC .......... A61M 16/0488; A61M 16/0475; A61M 16/04; A61M 16/0402; A61M 16/0427; A61M 25/0023; A61M 25/00; A61M 25/0015; A61M 25/0172
USPC ...................................... 128/207.14; 600/120
See application file for complete search history.

(56) References Cited

U.S. PATENT DOCUMENTS

| | | | | |
|---|---|---|---|---|
| 4,385,629 A | * | 5/1983 | Wolf, Jr. .......... | A61M 16/0463 128/207.14 |
| 5,477,851 A | * | 12/1995 | Callaghan ......... | A61M 16/0409 128/200.23 |
| 2007/0208302 A1 | * | 9/2007 | Webster ............ | A61M 25/0041 604/103.04 |

OTHER PUBLICATIONS

Brimacombe, J. (1993), The split laryngeal mask airway. Anaesthesia, 48: 639. doi: 10.1111/j.1365-2044.1993.tb07144.x.

* cited by examiner

*Primary Examiner* — Peter S Vasat
*Assistant Examiner* — Margaret Luarca
(74) *Attorney, Agent, or Firm* — Sughrue Mion, PLLC

(57) ABSTRACT

An endotracheal tube comprising a flexible hollow tube with a spiral slit traversing a substantial length of the tube. The slit has edges that separate to create an opening by which the tube may be spiral wound onto a medical device, such as a fiber optic bronchoscope, that is in use in a pharynx passage. The angle of the slit is preferably in the range of 30-60 degrees.

9 Claims, 1 Drawing Sheet

SPIRAL SLIT ENDOTRACHEAL TUBE

FIELD OF THE INVENTION

This invention relates to a medical instrument and the use thereof that establishes a "duty channel" for continuous access and control of the airway during bronchoscopy procedures.

BACKGROUND OF THE INVENTION

The fiber optic bronchoscope is used to access the airway via entry through the nasopharynx or oropharynx with continued passage between the true vocal cords and then advancing caudally into the laryngo-tracheo-bronchial tree. Once airway placement is achieved the fiber optic bronchoscope facilitates the diagnostic and therapeutic collection of glandular secretions and/or tissue specimens, foreign bodies, or tumors using the suction channel for the additional placement of flexible biopsy forceps or flexible brushes or flexible needles under direct vision. The ease and safety with which the procedure is performed can be modified by the presence of unexpected anatomic variations and complications that may arise as the bronchoscope navigates the nasopharynx in search of the laryngeal orifice housing the true vocal cords between which the fiber optic bronchoscope will then enter the larynx.

During the procedure a complication or finding may necessitate removal and replacement of the fiber optic bronchoscope and continued control of the airway for rapid reestablishment of patency of the airway or need to be able to mechanically ventilate the lungs while the procedure using a fiber optic bronchoscope ensues to its completion. In order to accomplish these actions it would be necessary to place an endotracheal to able to accept the external diameter of the fiber optic bronchoscope.

The current state of the art would force removal of the fiber optic bronchoscope and either orotracheally intubate in the standard manner or precharge the fiber optic bronchoscope with an endotracheal tube over the fiber optic bronchoscope so that after the fiber optic bronchoscope tip has entered the trachea one can slide the endotracheal tube over the fiber optic bronchoscope and so control the airway and use the endotracheal tube as an access channel allowing removal and replacement of the fiber optic bronchoscope as deemed necessary without going through the cumbersome process followed to initiate airway access. Some of the complicating factors include bleeding, encountering foreign bodies of different shapes and anatomic features such as larynx and vocal cord anomalies or polypoid tumors larger than the caliber of the suction channel of the fiber optic bronchoscope.

Current options for airway management during such procedures include withdrawal of the bronchoscope and intubation of the patient by endotracheal tube including the use of an obturator (See: U.S. Pat. No. 4,960,122) as a guide. As can be appreciated, time is of the essence to maintain airway control and prevent inadequate ventilation and/or oxygenation. Once the patient is stabilized the fiber optic bronchoscopy would be re-started. However, any trauma that has occurred may result in changes to more poorly identifiable access to the laryngo-tracheo-bronchial tree arising from constriction or edema or cyanosis due to complicating hypoxemia such that insertion may be difficult or impossible because of the presence of inadequate anatomic definition.

SUMMARY OF THE INVENTION

Given the inadequacies in the present state of the art, a need exists to allow placement of an endotracheal tube to allow rapid and repeated withdrawal and reinsertion of the fiber optic bronchoscope. As a result of the possibility of cumbersome anatomic variations and the importance of time factors involved, the most expeditious manner of emergently placing the endotracheal tube depends on the ability to place the endotracheal tube without being forced to remove the fiber optic bronchoscope prior to the endotracheal tube placement.

This invention is a spiral slit endotracheal tube that allows the placement of a "duty channel" that provides continuous access and control of the airway after it is spirally placed over the fiber optic bronchoscope. The spiral slit tube achieves this object without being forced to remove the fiber optic bronchoscope first. The practitioner could then use the "duty channel" to rapidly remove and reinsert the fiber optic bronchoscope as deemed necessary without having to deal with any possible impediments previously described.

The duty channel, if necessary, can then be used with the help of an endotracheal tube replacement obturator for the placement of a standard cuffed endotracheal tube or rigid bronchoscope. The spiral slit endotracheal tube has the significant advantage in that it allows continuous maintenance of access and control of the airway.

The spiral slit endotracheal tube is made of the same material already used to manufacture standard endotracheal tubes. This is typically a 6-8.5 mm ID plastic tube and a suitable length of about 30 cm or less. In accordance with this invention it has to have a helical slit cut through to the tube lumen at a continuum throughout a substantial portion of its length. The angle of the helix is determined as a function of the wall thickness of the tube and the stiffness of the material to allow ready winding over the bronchoscope to be stable and substantially sealed once mounted. Typically, the helix angle can be in the range of 30-60 degrees angled to the circular base to create a through spiral slit. The edge of the slit preferably has an angled finish so that when the slit edges are coapted it does not leave a grooved surface. When the spiral slit edges are coapted, the cylindrical tube created typically has an internal diameter of 6-8 mm and a length of about 22-30 cm for an adult size. A device for pediatric use would be sized appropriately smaller.

In operation, the spiral slit endotracheal tube is placed over the already inserted fiber optic bronchoscope by starting at the start of the angled slit winding the spiral slit over the shaft of the fiber optic bronchoscope until the internal wall is parallel to the axis of the fiber optic bronchoscope. The spiral slit endotracheal tube is secured with surgical tape to the face when the tip of the distal end of the spiral slit endotracheal tube is confirmed by the bronchoscope to be 2 cm rostral to the carina. Once in place a duty channel has been established. The bronchoscope may be removed and subsequently reinserted.

This invention will be described in greater detail by referring to the attached drawing and the description of the preferred embodiment that follows.

DESCRIPTION OF THE PREFERRED EMBODIMENT

Figure 1:
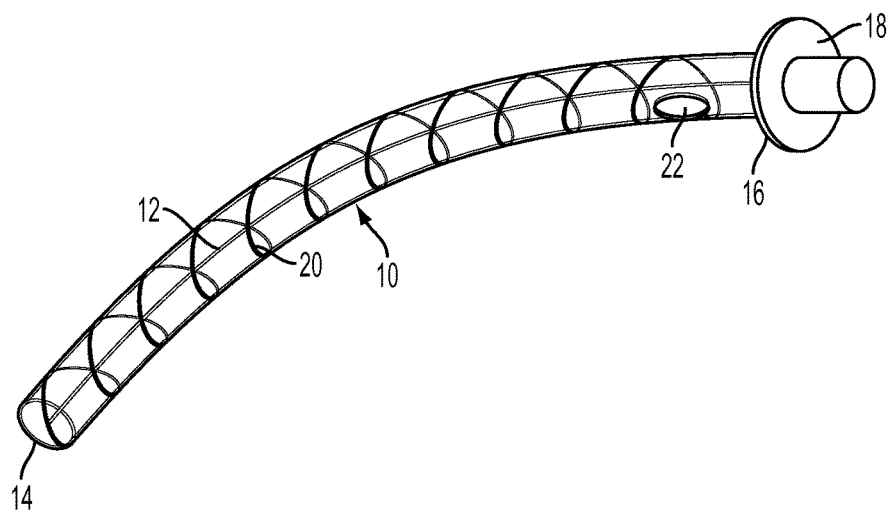
FIG. 1 is a perspective view of the spiral slit endotracheal tube according to this invention.

Referring now to FIG. 1, the spiral slit endotracheal tube 10 is a flexible plastic tube made from the same material normally used to manufacture conventional endotracheal tubes. Such devices are well known in the art and sold by companies such as Mallinckrodt. See for example, http://www.covidien.com/rms/brands/mallinckrodt The tube is generally made of clear plastic with an internal diameter of 6-8 mm. It will be understood that this size may be varied as a function of patient use. Thus, a device for pediatric use would be sized appropriately smaller. Conventionally, the tube is made with a radiopaque line 12. It has a distal end 14 which is rounded, tapered or otherwise smoothed to facilitate entry. The distal end may be blunt, as illustrated, or angled. The proximal end has a connector piece 16 that is inserted into the tube and includes a stop plate 18 which also provides surfaces for securing holding the tube. The tube 10 optionally has a side port 22.

In accordance with this invention, the tube 10 has a spiral slit 20 running from the distal end 14 to the zone near the side port 22. The slit 20 allows the sidewall of the tube to be separated such that the tube can be "wound" onto a bronchoscope. The angle of the helix is chosen to facilitate this mounting of the tube and then close, yet not be so loose that the tube does not remain in position. Typically the angle of the helix is in the range of 30-60 degrees. The walls of the slit may themselves be angled or tapered to allow spreading and then secure closing after mounting over the bronchoscope.

Figure 2:
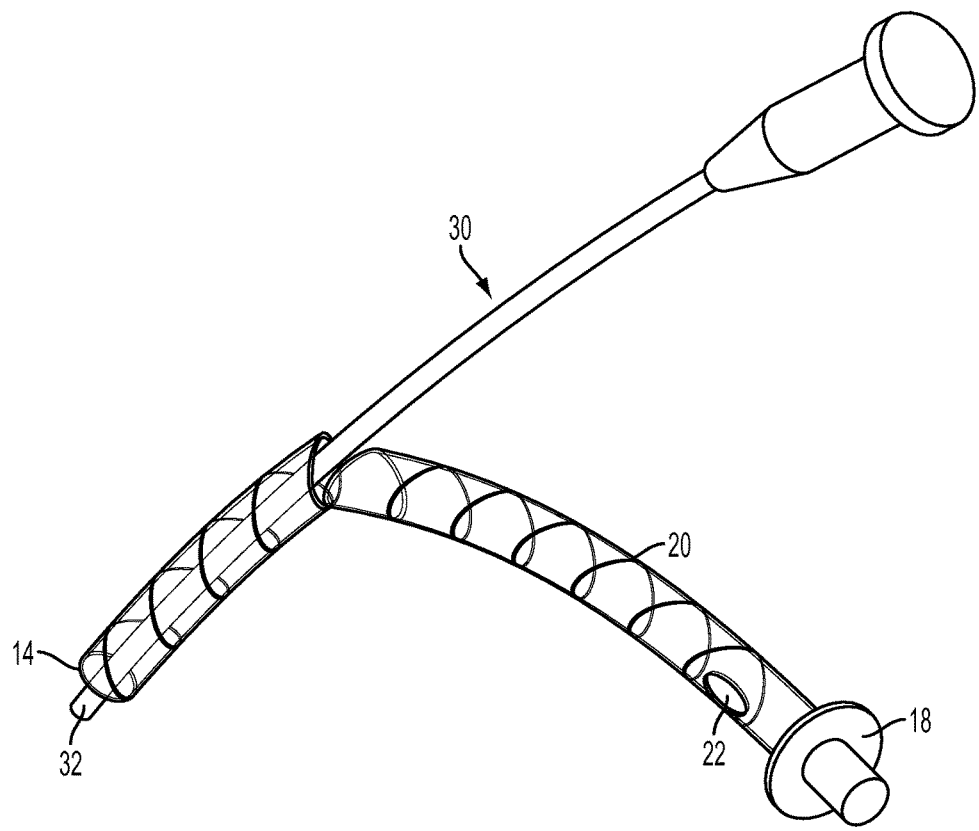
FIG. 2 is a perspective view illustrating how the tube of FIG. 1 is wound over a bronchoscope.

Referring now to FIG. 2, the operation of the device according to this invention will be described. A bronchoscope 30 has already been inserted either through the nasopharynx or oropharynx and the distal end 32 is advanced caudally into the laryngo-tracheo-bronchial tree. As mentioned, this device is conventionally used for both diagnostic and therapeutic purposes. During such procedures it is sometimes necessary to maintain control of the airway without first removing the bronchoscope. Starting at the distal end 14, the endotracheal tube 10 is spiral wound over the bronchoscope 30 at a location where the clinician has access to stabilize the scope and by tactile action spread the slit over it. Once the distal end 14 is circumferentially mounted, the rest of the tube 10 is spirally wound on and the tube 10 advances on the bronchoscope 30. When the tube 10 advances to the side port 22, mounting is complete and the stop plate 18 is properly located. Thus, the side port 22 is preferably the egress point at the end of the winding process. The bronchoscope 30 may be then withdrawn as the airway is maintained by the tube 10.

In addition, the spiral slit endotracheal tube could provide a channel for completing endotracheal tube placement in cumbersome situations forcing the use of a fiber optic bronchoscope for establishing airway access. In this scenario, after winding on the spiral slit endotracheal tube over the fiber optic bronchoscope the fiber optic bronchoscope is withdrawn and replaced by the endotracheal tube replacement obturator and leaving the endotracheal tube replacement obturator within the laryngo tracheal tree a standard orotracheal tube can be placed over the endotracheal tube replacement obturator followed by removal of the endotracheal tube replacement obturator and leaving the standard endotracheal tube in place within the orotracheal airway. Finally, the endotracheal tube is secured and the cuff of the distal portion of the endotracheal tube is inflated in the standard manner so that the distal tip of the secured endotracheal tube is 2 cm rostral to the carina.

This invention is subject to other departures and modifications without departing from the essential scope thereof. For example, while the preferred embodiment has been described with respect to bronchoscope, the device according to this invention may be used with other endotracheal devices. An example is use with a replacement obturator to establish initial airway control for the subsequent placement of instruments and/or a tracheal tube. The rostral end having the connector piece 16 may serve an entry and exit point when using the spiral tube as a channel. The connector could then be fitted with a swiveling punctured rubber capped end (not illustrated).

Also, while the angle of the slit is preferably a helix, it is apparent that as a function of length and the material the angle may be adjusted within a wide range.

Having described my invention, I claim:

1. An endotracheal tube for use with a medical device disposed within a laryngo-tracheo-bronchial tree comprising: a flexible hollow tube, a spiral slit starting from a distal end and traversing a substantial length of said tube, said slit having edges that separate to create an opening, said endotracheal tube being configured to be spiral wound onto the medical device and to maintain airway control as the medical device is inserted and removed.

2. The endotracheal tube of claim 1, further comprising an end fitting at a proximal end of said tube.

3. The endotracheal tube of claim 1, wherein the angle of said spiral is in the range of 30-60 degrees.

4. The endotracheal tube of claim 1, wherein the edges of said slit are angled in a compatible manner to close and maintain an internal wall of said tube substantially smooth.

5. The endotracheal tube of claim 1, wherein the medical device is a fiber optic bronchoscope, and wherein said tube is mountable in a concentric manner over the bronchoscope.

6. The endotracheal tube of claim 1, further comprising an external flange at a proximal end of said tube.

7. The endotracheal tube of claim 1, further comprising an opening at a proximal end of said tube, the opening serving as an egress point after the tube is spirally wound on the medical device.

8. The endotracheal tube of claim 6, further comprising an opening at a proximal end of said tube, the opening being disposed just distal to said flange, and the opening having a size and shape sufficient to allow the medical device to exit or enter from the side of the endotracheal tube via the opening.

9. The endotracheal tube of claim 1, further comprising an opening at a proximal end of said tube in a sidewall of said tube, the opening have a size and shape sufficient to allow the medical device to exit or enter from the side of the endotracheal tube via the opening.

* * * * *